United States Patent [19]
Baker et al.

[11] Patent Number: 5,854,247
[45] Date of Patent: Dec. 29, 1998

[54] PIPERAZINE, PIPERIDINE AND TETRAHYDROPYRIDINE DERIVATIVES USEFUL AS 5-HT1 RECEPTER AGONISTS

[75] Inventors: Raymond Baker, Uley; Andrew Madin, Sawbridgeworth, both of Great Britain; Victor Guilio Matassa, Rome, Italy; Leslie Joseph Street, Harlow, Great Britain

[73] Assignee: Merck Sharp & Dohme Ltd., Hoddesdon, England

[21] Appl. No.: 849,385

[22] PCT Filed: Nov. 15, 1995

[86] PCT No.: PCT/GB95/02687

§ 371 Date: Jul. 21, 1997

§ 102(e) Date: Jul. 21, 1997

[87] PCT Pub. No.: WO96/16056

PCT Pub. Date: May 30, 1996

[30] Foreign Application Priority Data

Nov. 23, 1994 [GB] United Kingdom .................. 9423682

[51] Int. Cl.⁶ ..................... A61K 31/495; C07D 413/14
[52] U.S. Cl. ........................ 514/253; 544/368; 544/371
[58] Field of Search ..................................... 544/368, 371; 514/253

[56] References Cited

U.S. PATENT DOCUMENTS

| | | |
|---|---|---|
| 3,135,794 | 6/1964 | Archer . |
| 3,468,882 | 9/1969 | Laskowski . |

FOREIGN PATENT DOCUMENTS

| | | |
|---|---|---|
| 0 345 808 A1 | 12/1989 | European Pat. Off. . |
| 0 464 558 A1 | 1/1992 | European Pat. Off. . |
| 0 464 604 A2 | 1/1992 | European Pat. Off. . |
| 0 464 604 A3 | 1/1992 | European Pat. Off. . |
| 0 548 813 A1 | 6/1993 | European Pat. Off. . |
| WO 91/18897 | 12/1991 | WIPO . |
| WO93/2007 | 10/1993 | WIPO . |
| WO94/02477 | 2/1994 | WIPO . |

OTHER PUBLICATIONS

Brewster, K. et al, Chim. Ther. 1973, 8(2), pp. 169–172, abstract only.

Garuti, L. et al, Arch. Pharm. 1988, 321(7), pp. 377–383, abstract only.

Archibald, J.L. et al, J. Med. Chem. 1974, 17(7), pp. 745–747, abstract only.

Primary Examiner—Alan L. Rotman
Assistant Examiner—Charanjit S. Aulakh
Attorney, Agent, or Firm—Philippe L. Durette; Melvin Winokur

[57] ABSTRACT

A class of N-substituted piperazine, piperadine and tetrahydropyridine derivatives of formula (I), further substituted at the 4-position by an optionally substituted aryl-alkyl or heteroaryl-alkyl moiety, are selective agonists of $5\text{-HT}_1$-like receptors, being potent agonists of the human $5\text{-HT}_{1D\alpha}$ receptor subtype relative to the $5\text{-HT}_{1D\beta}$ subtype; they are therefore useful in the treatment and/or prevention of clinical conditions, in particular migraine and associated disorders, for which a subtype-selective agonist of $5\text{-HT}_{1D}$ receptors is indicated, whilst eliciting fewer side-effects, notably adverse cardiovascular events, than those associated with non-subtype-selective $5\text{-HT}_{1D}$ receptor agonists. In formula (I) Z represents $-SO_2NR^5R^6$, or a group of formula (b).

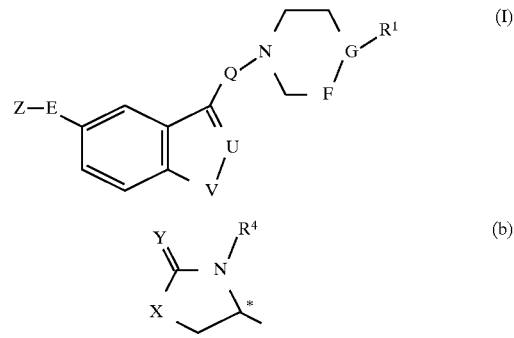

9 Claims, No Drawings

PIPERAZINE, PIPERIDINE AND TETRAHYDROPYRIDINE DERIVATIVES USEFUL AS 5-HT1 RECEPTER AGONISTS

This application is a 371 of PCT/GB95/02687, which is now published as WO96/16056 on May 30, 1996.

The present invention relates to a class of substituted piperazine, piperidine and tetrahydropyridine derivatives which act on 5-hydroxytryptamine 5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an optionally substituted arylalkyl or heteroaryl-alkyl substituent.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the piperazine, piperidine and tetrahydropyridine derivatives provided by the present invention.

Moreover, nowhere in the prior art available to date is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype.

The present invention provides a compound of formula I, or a salt or prodrug thereof:

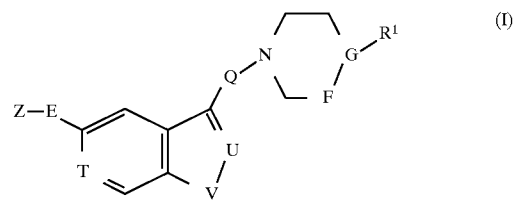

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (a), (b), (c) or (d):

(a)

(b)

(c)

-continued

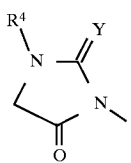

(d)

in which the asterisk * denotes a chiral center;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by a hydroxy group;

U represents nitrogen or C—$R^2$;

V represents oxygen, sulphur or N—$R^3$;

—F—G— represents —$CH_2$—N—, —$CH_2$—CH— or —CH=C—;

$R^1$ represents aryl($C_{1-6}$)alkyl or heteroaryl($C_{1-6}$)alkyl, either of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

The present invention also provides compounds of formula I above, and salts and prodrugs thereof, wherein $R^5$ and $R^6$ independently represent hydrogen, $C_{1-6}$ alkyl, trifluoromethyl, methylphenyl, or an optionally substituted aryl($C_{1-6}$)alkyl or heteroaryl($C_{1-6}$)alkyl group.

When $R^1$, $R^5$ or $R^6$ represents an aryl($C_{1-6}$)alkyl or heteroaryl($C_{1-6}$)alkyl group, this group may be optionally substituted, preferably on the aryl or heteroaryl moiety thereof, by one or more substituents. Examples of optional substituents thereon include halogen, cyano, trifluoromethyl, triazolyl, tetrazolyl, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl and allyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. For example, the compounds of formula I above wherein Z represents a group of formula (b) or (c) have a chiral centre denoted by the asterisk *, which may accordingly be in the (R) or (S) configuration. Where the compounds according to the invention possess two or more asymmetric centres, they may additionally exist as diastereoisomers. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by a hydroxy group giving rise, for example, to a 2-hydroxypropylene or 2-hydroxymethyl-propylene chain Q. Moreover, E may represent a chemical bond such that the moiety Z is attached directly to the benzo moiety of the central fused bicyclic heteroaromatic ring system.

Suitably, E represents a chemical bond or a methylene linkage.

Suitably, Q represents a propylene linkage.

The compound of formula I in accordance with the present invention is suitably an indole, benzofuran or benzthiophene derivative of formula IA, or an indazole derivative of formula IB:

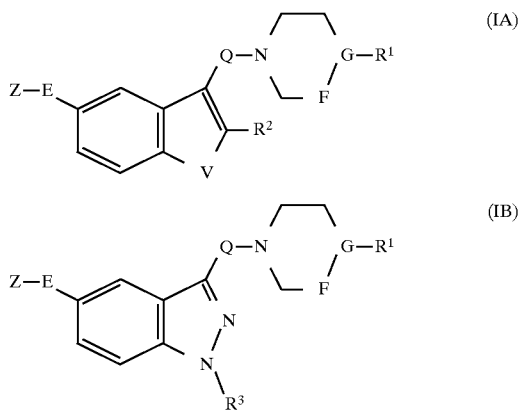

wherein Z, E, Q, V, F, G, $R^1$, $R^2$ and $R^3$ are as defined above. Preferably, the compounds according to the invention are indole derivatives of formula IC:

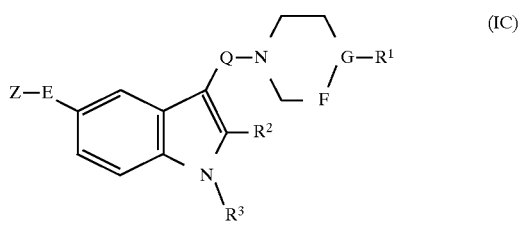

wherein Z, E, Q, F, G, $R^1$, $R^2$ and $R^3$ are as defined above, in particular wherein $R^2$ and $R^3$ are both hydrogen.

Suitable values for the substituent $R^1$ include benzyl, phenylethyl, furylmethyl, thienylmethyl, imidazolylmethyl and pyridylmethyl, any of which groups may be optionally substituted by one or more substituents selected typically from halogen, cyano, triazolyl, tetrazolyl, $C_{1-6}$ alkoxy, amino, $C_{2-6}$ alkylcarbonylamino, $C_{1-6}$ alkylsulphonylamino, aminocarbonylamino, aminosulphonyl and $C_{1-6}$ alkylaminosulphonylmethyl. Particular values of $R^1$ include benzyl, fluorobenzyl, difluorobenzyl, cyanobenzyl, methoxybenzyl, aminobenzyl, acetylamino-benzyl, aminosulphonyl-benzyl, phenylethyl, fluoro-phenylethyl, difluoro-phenylethyl, cyano-phenylethyl, triazolyl-phenylethyl, amino-phenylethyl, acetylamino-phenylethyl, aminocarbonylamino-phenylethyl, furylmethyl, thienylmethyl, imidazolylmethyl, pyridylmethyl and amino-pyridylmethyl.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, t-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylaminocarbonyloxy, cyano-methoxy, aminocarbonyl-methoxy, methylsulphonyl, phenylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (a), (b), (c) or (d) as defined above.

In a particular embodiment, Z represents $-SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (b) in which $R^4$ is hydrogen or methyl. In a subset of this embodiment, X and Y both represent oxygen. In a particular aspect of this subset, the chiral centre denoted by the asterisk * is in the (S) configuration.

A particular sub-class of compounds according to the invention is represented by the compounds of formula IIA, and salts and prodrugs thereof:

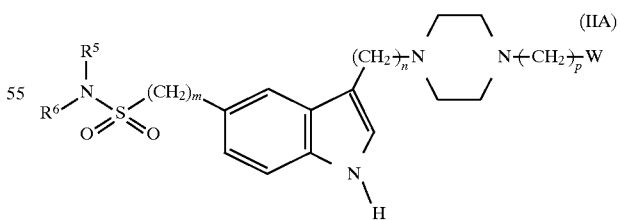

wherein m is zero, 1, 2 or 3, preferably zero or 1;

n is 2, 3, 4 or 5, preferably 3 or 4;

p is 1, 2 or 3;

$R^5$ and $R^6$ are as defined with reference to formula I above; and

W represents a group of formula (Wa), (Wb) or (Wc):

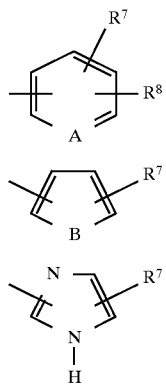

in which

A represents CH or nitrogen;

B represents oxygen, sulphur, NH or N-methyl; and $R^7$ and $R^8$ independently represent hydrogen, halogen, cyano, trifluoromethyl, triazolyl, $C_{1-6}$ alkoxy, $C_{2-6}$ alkylcarbonyl, amino, $C_{1-6}$ alkylamino, di($C_{1-6}$) alkylamino, $C_{2-6}$ alkylcarbonylamino, $C_{1-6}$ alkylsulphonylamino, aminocarbonylamino or $C_{1-6}$ alkylaminosulphonylmethyl.

Particular values of $R^5$ and $R^6$ with reference to formula IIA above include hydrogen and $C_{1-6}$ alkyl, especially hydrogen or methyl. Suitably, one of $R^5$ and $R^6$ represents hydrogen and the other represents hydrogen or methyl.

Particular values of $R^7$ include hydrogen, fluoro, cyano, triazolyl, methoxy, amino, acetylamino and aminocarbonylamino, especially hydrogen, fluoro or acetylamino.

Suitably, $R^8$ represents hydrogen or fluoro.

In a particular aspect, $R^8$ is hydrogen.

Another sub-class of compounds according to the invention is represented by the compounds of formula IIB, and salts and prodrugs thereof:

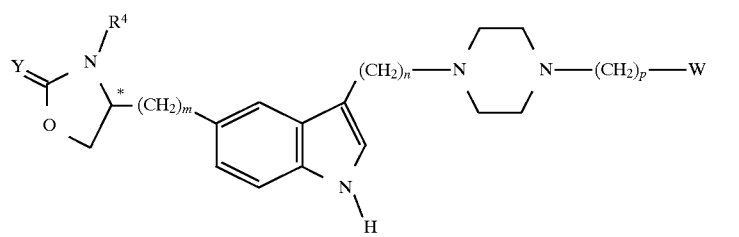

wherein the asterisk * denotes a chiral centre;

$R^4$ and Y are as defined with reference to formula I above; and m, n, p and W are as defined with reference to formula IIA above.

Particular values of $R^4$ with reference to formula IIB above include hydrogen and methyl, especially hydrogen.

Preferably, Y in formula IIB is oxygen.

Preferably, the chiral centre denoted by the asterisk * in formula IIB is in the (S) configuration.

Specific compounds within the scope of the present invention include:

1-[3-(5-(N-methylaminosulphonylmethyl)-1H-indol-3-yl) propyl]-4-[2-(4-(acetylamino)phenyl)ethyl]piperazine;

(S)-4-[3-(3-(4-(2-(3,4-difluorophenyl)ethyl)piperazin-1-yl) propyl)-1H-indol-5-ylmethyl]oxazolidin-2-one;

(S)-4-[3-(3-(4-(2-(3,4-difluorophenyl)ethyl)piperazin-1-yl) propyl)-1H-indol-5-ylmethyl]-3-methyloxazolidin-2-one; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein —F—G— represents —CH$_2$—N— may be prepared by a process which comprises N-alkylation of a compound of formula III:

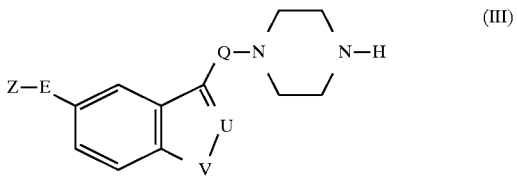

wherein Z, E, Q, U and V are as defined above.

Attachment of the R$^1$ moiety to the compounds of formula III may conveniently be effected by standard alkylation techniques, for example by treatment with an aryl(C$_{1-6}$)alkyl or heteroaryl(C$_{1-6}$)alkyl halide such as benzyl iodide, typically under basic conditions, e.g. sodium hydride in N,N-dimethylformamide, or triethylamine in acetonitrile. Alternatively, the R$^1$ moiety may conveniently be attached by a reductive alkylation procedure, which comprises treating the required compound of formula III as defined above with the appropriate aldehyde, e.g. benzaldehyde, in the presence of a reducing agent such as sodium cyanoborohydride.

The compounds of formula III above wherein U represents C—R$^2$ and V represents N—R$^3$, corresponding to the indole derivatives of formula IC as defined above wherein —F—G— represents —CH$_2$—N— and R$^1$ is hydrogen, may be prepared by a process which comprises reacting a compound of formula IV:

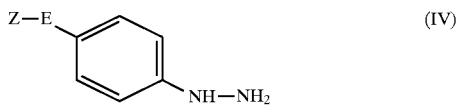

wherein Z and E are as defined above; with a compound of formula V, or a carbonyl-protected form thereof:

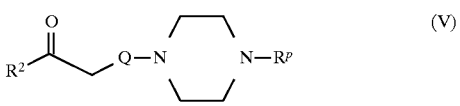

wherein R$^2$ and Q are as defined above, and R$^p$ represents an amino-protecting group; followed, where required, by N-alkylation by standard methods to introduce the moiety R$^3$; with subsequent removal of the amino-protecting group R$^p$.

The reaction between compounds IV and V, which is an example of the well-known Fischer indole synthesis, is suitably carried out by heating the reagents together under mildly acidic conditions, e.g. 4% sulphuric add at reflux.

Suitable carbonyl-protected forms of the compounds of formula V include the dimethyl acetal or ketal derivatives.

The protecting group R$^p$ in the compounds of formula V is suitably an alkoxycarbonyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

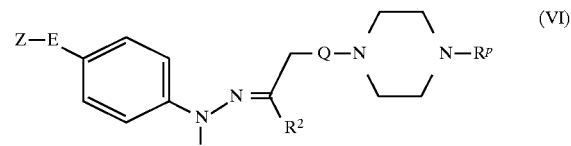

wherein Z, E, Q, R$^2$ and R$^p$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

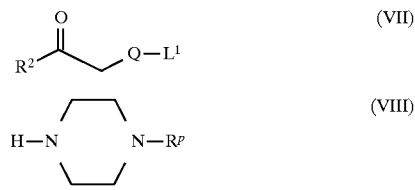

wherein Q, R$^2$ and R$^p$ are as defined above, and L$^1$ represents a suitable leaving group.

The leaving group L$^1$ is suitably a halogen atom, e.g. chlorine or bromine.

Where L$^1$ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein U represents C—R$^2$ and V represents N—R$^3$—i.e. the indole derivatives of formula IC as defined above—may alternatively be prepared by a process which comprises reacting a compound of formula IV as defined above with a compound of formula IX, or a carbonyl-protected form thereof:

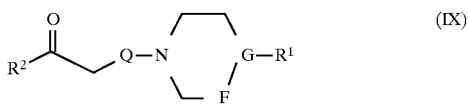

wherein Q, F, G, R$^1$ and R$^2$ are as defined above; under conditions analogous to those described above for the reaction between compounds IV and V; followed, where required, by N-alkylation by standard methods to introduce the moiety R$^3$.

As for the compounds of formula V, suitable carbonyl-protected forms of the compounds of formula IX include the dimethyl acetal or ketal derivatives.

As with that between compounds IV and V, the Fischer reaction between compounds IV and IX may be carried out in a single step, or may proceed via an initial non-cyclising step at a lower temperature to give an intermediate of formula X:

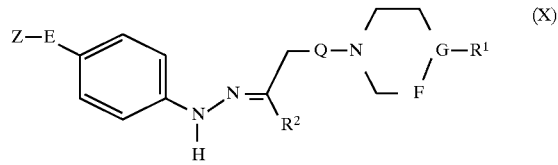

wherein Z, E, Q, F, G, R$^1$ and R$^2$ are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

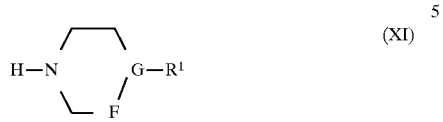

(XI)

wherein F, G and $R^1$ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

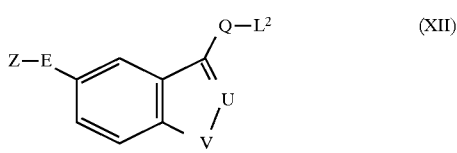

(XII)

wherein Z, E, Q, U and V are as defined above, and $L^2$ represents a suitable leaving group; followed by removal of the amino-protecting group RP.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, optionally in the presence of a cosolvent such as acetonitrile, typically in the presence of a base such as sodium carbonate or potassium carbonate, and optionally with the addition of sodium iodide.

In one representative approach, the compounds of formula XI wherein U represents CH, V represents NH and $L^2$ represents a mesyloxy or tosyloxy group may be prepared by the sequence of steps illustrated in the following reaction scheme (cf. Larock and Yum, *J. Am. Chem. Soc.*, 1991, 113, 6689):

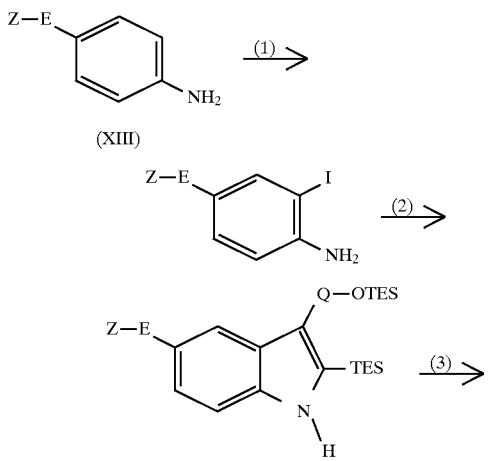

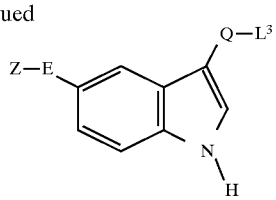

wherein Z, E and Q are as defined above, $L^3$ represents mesyloxy or tosyloxy, and TES is an abbreviation for triethylsilyl.

In Step 1 of the reaction scheme, the aniline derivative XIII is treated with iodine monochloride, typically in methanol or acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula XII wherein U represents CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative IV, typically the hydrochloride salt, in an inert solvent such as aqueous ethanol. The resulting hydrazide derivative can then be cyclised by treatment with a Lewis acid such as zinc chloride, in a solvent such as 1,2-dimethoxyethane, suitably at the reflux temperature of the solvent.

In a further procedure, the compounds of formula III above wherein U represents nitrogen and V represents N—$R^3$, corresponding to the indazole derivatives of formula IB as defined above wherein —F—G— represents —CH$_2$—N— and $R^1$ is hydrogen, may be prepared by a process which comprises cyclising a compound of formula XIV:

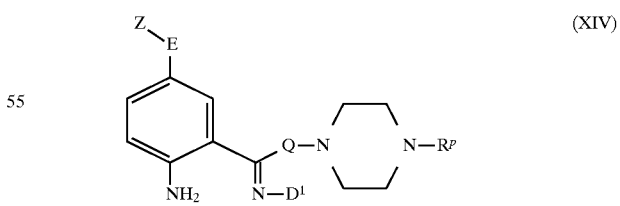

(XIV)

wherein Z, E, Q and RP are as defined above, and $D^1$ represents a readily displaceable group; followed, where required, by N-alkylation by standard methods to introduce the moiety $R^3$; with subsequent removal of the amino-protecting group $R^P$.

Similarly, the compounds of formula I wherein U represents nitrogen and V represents N—$R^3$—i.e. the indazole derivatives of formula IB as defined above—may be prepared by a process which comprises cyclising a compound of formula XV:

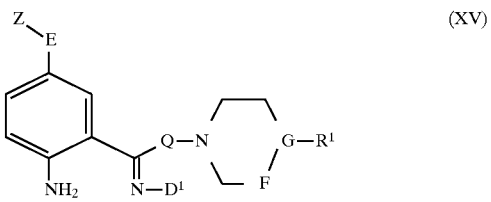

(XV)

in which Z, E, Q, F, G, $R^1$ and $D^1$ are as defined above; followed, where required, by N-alkylation by standard methods to introduce the moiety $R^3$.

The cyclisation of compounds MV and XV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIV and XV suitably represents a $C_{1-4}$ alkanoyloxy group, preferably acetoxy. Where $D^1$ represents acetoxy, the desired compound of formula XIV or XV may be conveniently prepared by treating a carbonyl compound of formula XVI:

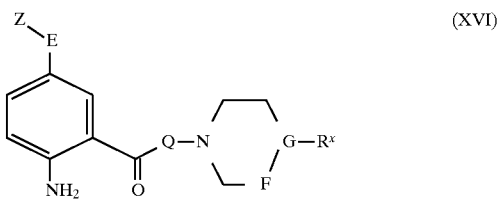

(XVI)

wherein Z, E, Q, F and G are as defined above, and $R^x$ corresponds to the group $R^1$ as defined above, or $R^x$ represents an amino-protecting group as defined for $R^p$ when —F—G— represents —$CH_2$—N—; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XVI may conveniently be prepared by ozonolysis of the corresponding indole derivative of formula XVII:

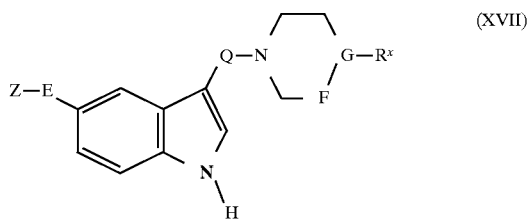

(XVII)

wherein Z, E, Q, F, G and $R^x$ are as defined above; followed by a reductive work-up, advantageously using dimethylsulphide.

The indole derivatives of formula XVII may be prepared by methods analogous to those described in the accompanying Examples, or by procedures well known from the art.

In a still further procedure, the compounds of formula III above wherein U represents C—$R^2$ and V represents oxygen or sulphur, corresponding to the benzofuran or benzthiophene derivatives of formula IA wherein V is oxygen or sulphur respectively, —F—G— represents —$CH_2$—N— and $R^1$ is hydrogen, may be prepared by a process which comprises cyclising a compound of formula XVIII:

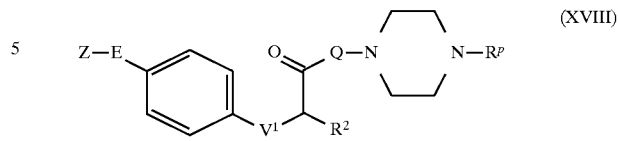

(XVIII)

wherein Z, E, Q, $R^2$ and $R^p$ are as defined above, and $V_1$ represents oxygen or sulphur; followed by removal of the amino-protecting group $R^p$.

Similarly, the compounds of formula I wherein U represents C—$R^2$ and V represents oxygen or sulphur—i.e. the benzofuran or benzthiophene derivatives of formula IA above—may be prepared by a process which comprises cyclising a compound of formula XIX:

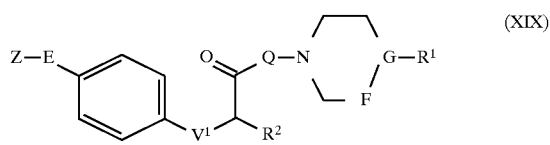

(XIX)

wherein Z, E, Q, F, G, $R^1$, $R^2$ and $V_1$ are as defined above.

The cyclisation of compounds XVIII and XIX is conveniently effected by using polyphosphoric acid or a polyphosphate ester, advantageously at an elevated temperature.

The compounds of formula XVII and XIX may be prepared by reacting a compound of formula XX with a compound of formula XXI:

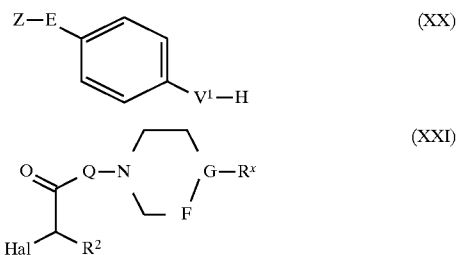

(XX)

(XXI)

wherein Z, E, Q, F, G, $R^2$, $V_1$ and $R^x$ are as defined above, and Hal represents a halogen atom.

The reaction is conveniently effected in the presence of a base such as sodium hydroxide.

The hydroxy and mercapto derivatives of formula XX may be prepared by a variety of methods which will be readily apparent to those skilled in the art.

The hydrazine derivatives of formula IV above may be prepared by methods analogous to those described in EP-A-0548813 and WO-A-91/18897, as also may the aniline derivatives of formula XIII.

Where they are not commercially available, the starting materials of formula VII, VIII, XI and M may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein —F—G— represents —CH=C— initially obtained may be readily converted into the corresponding compound wherein —F—G— represents —$CH_2$—CH— by conventional catalytic hydrogenation procedures. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000g at 4° C. for 11 min. The pellet was then resuspended in 50 mM Tris-HCl followed by a 10 min incubation at 37° C. Finally the tissue was recentrifuged at 48,000g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [3H]-5-HT for saturation studies or 2–5 nM [3H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/ 0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl -EGTA buffer (composition in mM: Tris HCl 10, EGTA 1, pH 8.0 at room temperature) and incubated on ice for 30–60 min. The tissue was then centrifuged at 20,000g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. The $EC_{50}$ values for the 5-$HT_{1D\alpha}$ receptor obtained for the compounds of the accompanying Examples were below 500 nM in each case. Moreover, the compounds of the accompanying Examples were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000g, 4° C. for 15 min. The pellet was then resuspended in ice cold 20 mM HEPES containing 0.1 mM EDTA, pH 7.4 at room temperature and recentrifuged at 40,000g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 μg protein/ml for the 5-$HT_{1D\alpha}$ receptor transfected cells and 40–50 μg protein/ml for the 5-$HT_{1D\beta}$ receptor transfected cells. The membrane suspension was then incubated, in a volume of 1 ml, with GDP (100 μM for 5-$HT_{1D\alpha}$ receptor transfected cells, 30 μM for the 5-$HT_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. The $EC_{50}$ values for the 5-$HT_{1D\alpha}$receptor obtained for the compounds of the accompanying Examples were below 500 nM in each case. Moreover, the compounds of the accompanying Examples were found to possess at least a 10-fold selectivity for the 5-$HT_{1D\alpha}$receptor subtype relative to the 5-$HT_{1D\beta}$subtype.

EXAMPLE 1

1-(3-[5-(N-(Methyl)aminosulphonylmethyl)-1H-indol-3-yl]propyl)-4-[2-(4-( acetylamino)phenyl) ethyl]piperazine. 2.0 Hydrogen Oxalate. Monohydrate 1. Intermediate 1:4-(N-(Methyl)aminosulphonylmethyl)-phenylhydrazine hydrochloride a) 1-(N-(Methyl)aminosulphonylmethyl)-4-nitrobenzene A mixture of 4-nitrobenzyl bromide (100.0 g 0.46 mol), sodium sulphite (84.8g, 0.67 mol) and water (316 ml) was heated at 90° C. for 5 h. The solution was cooled and the resultant solid filtered and washed with diethyl ether. The product was dried under vacuum at 60° C. (95 g, 86%). Phosphorus pentachloride (78 g, 0.375 mol) was added to sodium 4-nitrobenzyl sulphonate (60 g, 0.25 mol) and the mixture heated at 90° C. for 2 h. The mixture was cooled and volatile material removed under vacuum. The residue was dissolved in dichloromethane (500 ml) and water (150 ml). The organic layer was separated, dried over anhydrous sodium sulphate, filtered and evaporated to give 4-nitrobenzyl sulphonyl chloride (48.9 g, 83%) which was pure by $^1$H NMR. Methylamine gas was bubbled through a solution of 4-nitrobenzyl sulphonyl chloride (37.9 g, 0.16 mol), in dichloromethane (325 ml), until uptake had ceased (0.5 h). The resulting solid was filtered, washed with $H_2$ and dried under vacuum to give the title-sulphonamide (32.5 g, 88%), $\delta$(250MHz, $D_6$-DMSO) 2.61 (3H, s, Me), 4.55 (2H, s, $CH_2$), 7.06 (1H, s, NH), 7.66 (2H, d, J=8.7Hz, Ar-H), 8.25 (2H, d, J=8.7Hz, Ar-H).

b) 4-(N-(Methyl)aminosulphonylmethyl) phenylhydrazine hydrochloride

A mixture of the preceding 4nitro-N-methylbenzene methane sulphonamide (28.86 g, 0.126 mol), $H_2$ (100 ml), ethanol (250 ml), 5N HCl (25 ml) and 10% Pd-C (3.0 g) was hydrogenated on a Parr shake apparatus at 50psi for 4 h. The catalyst was removed by filtration through celite and the solvents removed under vacuum. The residue was dissolved in water (200 ml) and basified with $K_2CO_3$. The precipitated product was filtered off, washed with water and hexane and dried under vacuum at 45° C. to give the desired aniline (21.45 g, 85%) which was pure by $^1$H NMR. The aniline (16.9 g, 84.5 mmol) was stirred as a suspension in concentrated hydrochloric acid (90 ml) at –10° C., and a solution of sodium nitrite (6.41 g, 93.0 mmol ) in water (30 ml) was added dropwise. After addition was complete, the mixture was stirred at –5° C. for 0.25 h and then filtered into a precooled flask. The solution was added dropwise to a cooled and stirred solution of $SnCl_2.2H_2$ (76 g, 0.338 mol) in concentrated hydrochloric acid (90 ml), at –5° C. The resulting suspension was warmed to room temperature, filtered and the solid product washed with diethyl ether and hexane. Drying in vacuo at 50° C. gave the title-hydrazine (8.3 g, 39%), $\delta$(250MHz, $D_2$) 2.72 (3H, s, Me), 4.46 (2H, s, $CH_2$), 7.07 (2H, d, J=8.7 Hz, Ar-H), 7.44 (2H, d, J=8.7 Hz, Ar-H).

2. Intermediate 2:1-(H)-4-[2-(4-(acetylamino) phenyl)ethyl]piperazine

2-[4-(Acetylamino)phenyl]ethyl bromide (2.6 g, 10.7 mmol) was added to a mixture of N-tert-butyloxycarbonyl piperazine (2.0 g, 10.7 mmol) and $K_2CO_3$ (3.0 g, 21.7 mmol), in IPA (100 ml), and heated at 100° C. for 16 h. The mixture was filtered and the filtrate evaporated under vacuum. The residue was taken up into ethyl acetate and washed with $H_2O$. The aqueous phase was extracted with EtOAc and the combined extracts dried ($Na_2SO_4$/$MgSO_4$) and evaporated. The crude product was chromatographed on silica gel eluting with ethyl acetate to give 1-tert-butyloxycarbonyl-4-[2-(4-(acetylamino)phenyl)ethyl] piperazine (1.8 g, 49%) which was shown to be pure by $^1$H NMR. A solution of the preceding N-Boc piperazine (1.8 g, 5.19 mmol) in 99% formic acid (30 ml) was stirred at room temperature for 16 h. The solvent was removed under vacuum and the product chromatographed on silica gel eluting with $CH_2Cl_2$/ MeOH/$NH_3$ (50:8:1) to give the title-piperazine (1.3 g, 100%) $\delta$(250 MHz, $D_6$-DMSO) 2.01 (3H, s, Me), 2.26–2.72 (12H, m, 6 of $CH_2$), 7.12 (2H, d, J=8.5 Hz, Ar-H), 7.46 (2H, d, J=8.5 Hz, Ar-H), 9.85 (1H, s, NH).

3. Intermediate 3:3-[5-(N-(Methyl)aminosulphonylmethyl)-1H-indol-3-yl]propan-1-ol A solution of Intermediate 1 (5.0 g, 19.9 mmol) and 3,4-dihydro-2H-pyran (2.0 g, 23.8 mmol), in EtOH/$H_2$ (116 ml/116 ml), was stirred at room temperature for 16 h. The mixture was basified to pH10 by addition of $K_2CO_3$ and the ethanol removed under vacuum. The aqueous was extracted with EtOAc (4×250 ml), dried ($Na_2SO_4$) and evaporated. The residue was chromatographed on silica gel eluting with $CH_2Cl_2$/MeOH/$NH_3$ (95:5:0.5) to give the desired hydrazide (3.3 g, 55.6%). A solution of the hydrazide (3.27 g, 10.94 mmol) in DME (65 ml) was added portionwise to a solution of zinc chloride (7.5 g, 55.0 mmol) in DME (350 ml) and the mixture refluxed for 34 h. The solvent was evaporated to half volume, EtOAc (250 ml) added and washed with $H_2O$ (x1) and brine (x1). The organic was dried ($Na_2SO_4$/$MgSO_4$) and evaporated and the residue chromatographed on silica gel eluting with $CH_2Cl_2$/MeOH/$NH_3$ (95:5:0.5) to give Intermediate 3 (0.85 g, 28%), $\delta$(250 MHz, $D_6$-DMSO) 1.74–1.85 (2H, m, $CH_2$), 2.53 (3H, d, J=4.3 Hz, Me), 2.70 (2H, t, J=7.4 Hz, $CH_2$), 3.47 (2H, dd, J=5.2 and 7.4 Hz, $CH_2$), 4.34 (2H, s, $CH_2$) 4.46 (1H, t, J=5.2HZ, OH), 6.77 (1H, br q, J=4.3 Hz, NH), 7.06 (1H, dd, J=2.1 and 8.3 Hz, Ar-H), 7.12 (1H, d, 2.1 Hz, Ar-H), 7.31 (1H, d, 8.3 Hz, Ar-H), 7.50 (1H, s, Ar-H), 10.80 (1H, s, NH).

4. 1-(3-[5--(Methyl)aminosulphonylmethyl)-1H-indol-3-yl] propyl)-4-[2-(4-(acetylamino)phenyl)ethyl]piperazine. 2.0 Hydrogen Oxalate. Monohydrate Methane sulphonyl chloride (0.12 g, 1.07 mmol) was added to a solution of Intermediate 3 (0.2 g, 0.71 mmol) and triethylamine (0.143 g, 1.4 mmol) in $CH_2Cl_2$/$CH_3CN$ (5 ml/5 ml), at 0° C. The mixture was warmed to room temperature and stirred for 1 h before adding ethyl acetate (30 ml) and washing the solution with saturated $NaHCO_3$ solution (x1) and brine (x1). The organic was dried ($MgSO_4$) and evaporated. To a solution of the resultant residue in IPA (25 ml) and $CH_3CN$ (3 ml) was added Intermediate 2 (0.36 g, 1.6 mmol) and $Na_2CO_3$ (0.12 g, 1.09 mmol). The mixture was heated at reflux for 8 h then cooled to room temperature and filtered. The solvent was removed under vacuum and the residue chromatographed on silica gel eluting with $CH_2Cl_2$/ $MeOH/NH_3$ (90:8:1) to give the title-indole (0.208 g, 57%). The 2.0 hydrogen oxalate monohydrate salt was prepared, mp 213°–215° C., (Found: C, 52.54, H, 6.04, N, 9.50. $C_{27}H_{37}N_5SO_3$.2 $(C_2H_2O_4)$.1$H_2O$ requires C, 52.46, H, 6.11, N, 9.87%), m/e 511 (M)$^+$, $\delta$(360 MHz, $D_6$-DMSO) 1.88–2.00 (2H, m, $CH_2$), 2.02 (3H, s, NHCO<u>Me</u>), 2.54 (3H, d, J=4.1 Hz, $SO_2$NH<u>Me</u>), 2.68–3.12 (16H, m, 8 of $CH_2$), 4.34 (2H, s, $CH_2$), 6.79 (1H, br q, $SO_2$N<u>H</u>Me), 7.09 (1H, dd, J=2.0 and 8.3 Hz, Ar-H), 7.15 (2H, d, J=8.5 Hz, Ar-H), 7.18 (1H, d, J=2.0 Hz, Ar-H), 7.33 (1H, d, J=8.3 Hz, Ar-H), 7.48 (2H, d, J=8.5Hz, Ar-H), 7.51 (1H, s, Ar-H), 9.87 (1H, s, NH), 10.89 (1H, s, NH).

EXAMPLE 2

(S)-4-(3-(3-(4-(2-(3,4-Difluorophenyl)ethyl) piperazin-1-yl)propyl)-1H-indol-5-ylmethyl) oxazolidin-2-one. 2.0 Hydrogen Oxalate. 0.25 Hydrate 1. (S)-4-(4-Aminobenzyl)-1,3-oxazolidin-2-one Prepared as described in WO 91/18897.

2. (S)-4-(3-Iodo-4-aminobenzyl)-1.3-oxazolidin-2-one

A solution of iodine monochloride (4.84 g, 29.8 mmol) in methanol (35 ml) was added dropwise to a stirred mixture of (S)-4-(4-aminobenzyl)-1,3-oxazolidin-2-one (5.2 g, 27.0 mmol) and calcium carbonate (5.42 g, 54.2 mmol) in methanol (1 15 ml), at −40° C. The reaction was allowed to warm to room temperature and stir for 16 h. The solvent was removed under reduced pressure, the residue taken up into ethyl acetate (300 ml) and washed with 20% aqueous sodium thiosulphate (100 ml). The organic layer was separated, washed with water (50 ml) and brine (50 ml), dried ($Na_2SO_4$) and evaporated. The crude product was chromatographed on silica gel eluting with $CH_2Cl_2$/MeOH/ 98:2 to give the title-iodoaniline (3.88, 45%), $\delta$(250 MHz, $D_6$-DMSO) 2.55–2.60 (2H, m, $CH_2$), 3.90–3.99 (2H, m, $CH_2O$), 4.19–4.28 (1H, m, C<u>H</u>NH), 5.09 (2H, s, $NH_2$), 6.69 (1H, d, J=8.2 Hz, Ar-H,), 6.95 (1H, dd, J=1.9 and 8.2 Hz, Ar-H), 7.44 (1H, d, J=1.9 Hz, Ar-H). 7.74 (1H, s, NH).

3. Intermediate 4:(S)-4-(3-(3-Hydroxypropyl)-1H-indol-5-ylmethyl)-oxazolidin-2-one A mixture of (S)-4-(4-amino-3-iodo-benzyl)-1,3-oxazolidin-2-one (4.0 g, 12.6 mmol), 1-triethylsilyl-5-(triethylsilyloxy)pent-1-yne (6.0 g, 19.2 mmol), lithium chloride (540 mg, 12.7 mmol), sodium carbonate (6.7 g, 63 mmol) and triphenylphosphine (670 mg, 2.6 mmol) in dry dimethylformamide was deoxygenated. Palladium (II) acetate (300 mg, 1.3 mmol) was then added and the mixture deoxygenated for a further 5 minutes. The reaction was then stirred and heated at 100° C. for 18 hours. Upon cooling, the dimethylformamide was removed in vacuo. The residue was partitioned between EtOAc/$H_2O$. The aqueous was further extracted with EtOAc (x2). The combined extracts were dried ($Na_2SO_4$), filtered and evaporated. The residue was taken up in tetrahydrofuran (150 ml) and treated with 2N hydrochloric acid (19 ml, 38 mmol). The mixture was stirred at room temperature for 24 hours. The reaction was cooled to 0° C. and quenched with saturated aqueous potassium carbonate. The tetrahydrofuran was removed in vacuo, and the aqueous was extracted with $CH_2Cl_2$ (x3). The combined extracts were dried ($Na_2SO_4$), filtered and evaporated. The residue was purified by chromatography on silica gel, eluting with 8→10% MeOH/$CH_2Cl_2$ to give the title indole (2.2 g, 64%) as a light brown solid, $\delta$(360 MHz, $d_6$-DMSO) 1.78–1.84 (2H, m), 2.69 (2H, t, J=7.5 Hz), 2.77 (1H, dd, J=13.5, 7.1 Hz), 2.89 (1H, d, J=13.5, 4.5 Hz), 3.44–3.49 (2H, m), 4.00–4.08 (2H, m), 4.19–4.24 (1H, m), 4.41 (2H, t, J=5.0 Hz, $CH_2OH$), 6.92 (1H, dd, J=8.3, 1.5 Hz, Ar-H), 7.06 (1H, d, J=2.1 Hz, ArH), 7.25 (1H, d, J=8.3 Hz, Ar-H), 7.35 (1H, s, Ar-H), 7.76 (1H, s), 10.65 (1H, br s, N–H).

4. (S)-4-(3-(3-(4-(2-(3,4-Difluorophenyl)ethyl)piperazin-1-yl)propyl)-1H-indol-5-ylmethyl)oxazolidin-2-one. 2.0 Hydrogen Oxalate. 0.25 Hydrate Methane sulphonyl chloride (130 μl, 1.7 mmol) was added dropwise to a stirred solution of the preceding alcohol (300 mg, 1.1 mmol) and triethylamine (460 μl, 3.3 mmol) in dry tetrahydrofuran (20 ml) at 0° C. under nitrogen. After 15 minutes at 0° C. the cooling bath was removed and the mixture was stirred at room temperature for 1 hour. The precipitate was removed by filtration (washing with tetrahydrofuran). The filtrate was evaporated (without heating), and the residue was partitioned between $CH_2Cl_2$/ $H_2O$. The organic layer was then washed with water (x1), brine (x1), then dried ($Na_2SO_4$), filtered and evaporated.

The mesylate from above was taken up in dry isopropanol (10 ml) and dry acetonitrile (10 ml). Potassium carbonate (460 mg, 3.3 mmol) was added, followed by a solution of 4-(2-(3,4-difluorophenyl)ethyl)piperazine (440 mg, 1.9 mmol) in dry isopropanol (5+5 ml). Finally sodium iodide (170 mg, 1.1 mmol) was added and the mixture was stirred and heated at reflux under nitrogen, protected from light, for 20 hours. Upon cooling, the volatiles were removed in vacuo and the residue partitioned between $CH_2Cl_2$/$H_2O$. The aqueous was further extracted with $CH_2Cl_2$ (x2). The combined extracts were dried ($Na_2SO_4$), filtered and evaporated. The residue was purified by chromatography on silica gel, eluting with $CH_2Cl_2$/MeOH/NH$_3$ (95:5:0.5→91:8:1) to give the title i7idole (291 mg, 55%) as a foam. The bishydrogen oxalate 0.25 hydrate was prepared Et$_2$O/MeOH: (Found: C, 55.77, H, 5.42, N, 8.12. $C_{27}H_{32}N_4O_2F_2$. 2$(C_2H_2O_4)$. 0.25 ($H_2O$) requires C, 55.81, H, 5.51, N, 8.40%), $\delta$(360 MHz, $d_6$-DMSO) 1.96–2.04 (2H, m), 2.7–3.2 (18H, m), 4.04–4.10 (2H, m), 4.24–4.30 (1H, m 6.95 (1H, d, J=9.6 Hz, Ar-H), 7.08–7.14 (2H, m, Ar-H), 7.24–7.38 (4H, m, Ar-H), 7.78 (1H, s, 10.77 (1H, s).

EXAMPLE 3

(S)-4-(3-(3-(4-(2-(3,4-Difluorophenyl)ethyl) piperazin-1-yl)propyl)-1H-indol-5-ylmethyl)-3-methyloxazolidin-2-one. 1.5 Hydrogen Oxalate 1. Intermediate 5:(S)-4-(4-Amino-3-iodobenzyl)-3-methyloxazolidin-2-one A solution of iodine monochloride (2.9 g, 17.9 mmol) in dry methanol (30 ml) was added dropwise to a stirred solution/suspension of (S)-4-(4-aminobenzyl)-3-methyloxazolidin-2-one (3.3 g, 16 mmol) (WO 91/18897) and calcium carbonate (3.2 g, 32 mmol) in dry methanol (100 ml), at −50° C. under nitrogen. Upon complete addition the mixture was maintained at −50° C. for 30 minutes, then allowed to warm to room temperature. The mixture was stirred at this temperature for 16 hours. The calcium carbonate was then removed by filtration (washing with methanol). Saturated aqueous sodium thiosulphate was added, then the methanol was removed in vacuo. The aqueous was extracted with dichloromethane (x3). The combined extracts were dried ($Na_2SO_4$), filtered and evaporated. The residue was purified by chromatography on silica gel, eluting with 1→2% MeOH/$CH_2Cl_2$ to give the title iodo-aniline (4.5 g, 85%), $\delta$(250 MHz, CDCl$_3$) 2.55 (1H, dd, J=13.8, 8.7 Hz), 2.88 (3H, s, CH$_3$), 2.95 (1H, dd, J=13.8, 4.6 Hz), 3.78–4.24 (5H, m, inc. NH2), 6.70 (1H, d, J=8.1 Hz, Ar-H), 6.93 (1H, dd, J=8.2, 2.1 Hz, Ar-H), 7.45 (1H,d, J=2.1 Hz, Ar-H).

21

2. Intermediate 6: (S)-4-(3-(3-Hydroxypropyl)-1H-indol-5-ylmethyl)-3-methyloxazolidin-2-one A mixture of the iodo-aniline (5.0 g, 15 mmol), 1-triethylsilyl-5-(triethylsilyloxy) pent-1-yne (7.1 g, 23 mmol), lithium chloride (640 mg, 15 mmol), sodium carbonate (7.9 g, 75 mmol) and triphenylphosphine (800 mg, 3 mmol) in dry dimethylformamide (100 ml) was deoxygenated. Palladium (II) acetate (340 mg, 1.5 mmol) was added and the mixture was deoxygenated for a further 5 minutes. The mixture was then stirred and heated at 100° C. under nitrogen for 18 hours. Upon cooling the dimethylformamide was removed in vacuo, and the residue was partitioned between EtOAc/$H_2O$. The aqueous was further extracted with EtOAc (x2). The combined extracts were dried ($Na_2SO_4$), filtered and evaporated.

The residue was taken up in tetrahydrofuran (150 ml) and treated with 2N hydrochloric acid (25 ml, 50 mmol) at room temperature. The mixture was stirred at this temperature for 20 hours. The reaction was then cooled to 0° C. and quenched with saturated aqueous potassium carbonate. The tetrahydrofuran was removed in vacuo and the aqueous was extracted with dichloromethane (x3). The combined extracts were dried ($Na_2SO_4$), filtered and evaporated. The residue was purified by chromatography on silica gel, eluting with 5% MeOH/$CH_2Cl_2$ to give the title indole (2.4 g, 58%) as a foam, δ (360 MHz, $CDCl_3$) 1.94–2.04 (2H, m), 2.77–2.90 (3H, m), 2.93 (3H, s, $CH_3$), 3.21 (1H, dd, J=13.7, 4.6 Hz), 3.73 (2H, t, J=6.3 Hz), 3.94–4.02 (1H, m), 4.06 (1H, dd, J=8.7, 6.0 Hz), 4.17 (1H, app t, J=8.5 Hz), 6.96 (1H, dd, J=8.3, 1.6 Hz, Ar-H), 7.02 (1H, d, J=2.2 Hz, Ar-H), 7.31 (1H, d, J=8.0 Hz, Ar-H), 7.38 (1H, s, Ar-H), 8.00 (1H, br s, N-H).

3. (S)-4-(3-(3-(4-(2-(3,4-Difluorophenyl)ethyl)piperazin-1-yl)propyl)-1H-indol-5-ylmethyl)-3-methyloxazolidin-2-one. 1.5 Hydrogen Oxalate Methane sulphonyl chloride (120 μl, 1.6 mmol) was added dropwise to a stirred solution of the homotryptol (300 mg, 1.04 mmol) and triethylamine (430 μl, 3.1 mmol), in dry tetrahydrofuran (20 ml), at 0° C. under nitrogen. After 15 minutes at 0° C. the cooling bath was removed and the mixture was stirred at room temperature for 1 hour. The precipitate was removed by filtration (washing with tetrahydrofuran). The filtrate was evaporated (without heating), and the residue was partitioned between $CH_2Cl_2$/$H_2O$. The organic layer was then washed with water (x1), brine (x1), then dried ($Na_2SO_4$), filtered and evaporated.

The mesylate from above was taken up in dry isopropanol (10 ml) and dry acetonitrile (10 ml). Potassium carbonate (460 mg, 3.3 mmol) was added, followed by a solution of 4-(2-(3,4-difluorophenyl)ethyl)piperazine (440 mg, 1.9 mmol) in dry isopropanol (5+5 ml). Finally, sodium iodide (170 mg, 1.1 mmol) was added and the mixture was stirred and heated at reflux for 18 hours, protected from light. Upon cooling the volatiles were removed in vacuo and the residue was partitioned between $CH_2Cl_2$/$H_2O$. The aqueous was further extracted with $CH_2Cl_2$ (x2). The combined extracts were dried ($Na_2SO_4$), filtered and evaporated. The residue was purified by chromatography on silica gel, eluting with $CH_2Cl_2$/MeOH/$NH_3$ (95:5:0.5) to give the title indole (350 mg, 68%) as a foam. The 1.5 hydrogen oxalate was prepared ($Et_2O$/MeOH): (Found C, 58.68, H, 5.86, N, 8.99. $C_{28}H_{34}N_4O_2F_2$.1.5 ($C_2H_2O$) requires C, 58.95, H, 5.90, N, 8.87%), δ(360 MHz, $d_6$-DMSO) 1.92–2.04 (2H, m), 2.7–3.2 (22H, m), 3.98–4.06 (2H, m), 4.12–4.20 (1H, m), 6.96 (1H, d, J=6.9 Hz, Ar-H), 7.08–7.16 (2H, m, Ar-H), 7.27–7.37 (4H, m, Ar-H), 10.79 (1H, br s, N-H).

22

We claim:

1. A compound of formula I, or a salt or prodrug thereof:

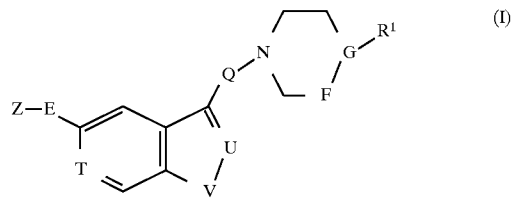

wherein

Z represents —$SO_2NR^5R^6$, or a group of formula (b),

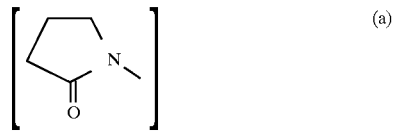

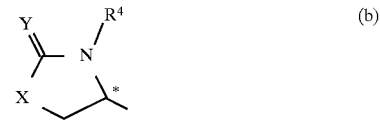

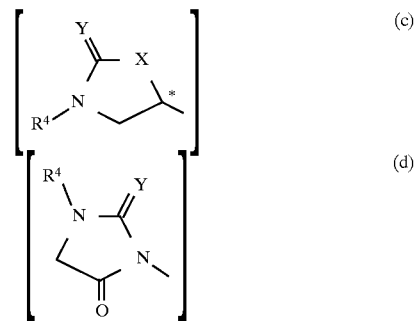

in which the asterisk * denotes a chiral centre;

X represents oxygen,

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by a hydroxy group;

T represents CH;

U represents nitrogen or C—$R^2$;

V represents oxygen, sulphur or N—$R^3$;

—F—G— represents —$CH_2$—N—, $R^1$ represents aryl($C_{1-6}$)alkyl or heteroaryl($C_{1-6}$)alkyl, either of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl ($C_{1-6}$)alkyl group; or $R^5$ and $R^6$, when linked through a nitrogen atom, together represent the residue of an optionally substituted azetidine, pyrrolidine, piperidine, morpholine or piperazine ring.

2. A compound as claimed in claim 1 wherein Z represents —$SO_2NR^5R^6$ in which $R^5$ and $R^6$ are as defined in claim 1.

3. A compound as claimed in claim 1 wherein Z represents a group of formula (b) as defined in claim 1.

4. A compound as claimed in claim 1 represented by formula IIA, and salts and prodrugs thereof:

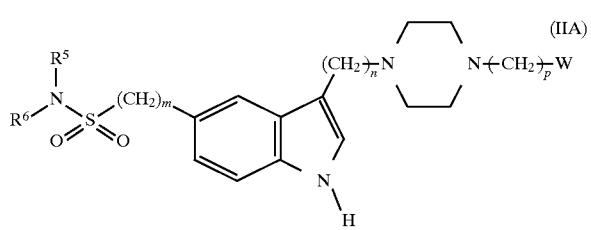

wherein
m is zero, 1, 2 or 3;
n is 2, 3, 4 or 5;
p is 1, 2 or 3;
$R^5$ and $R^6$ are as defined in claim 1; and
W represents a group of formula (Wa), (Wb) or (Wc):

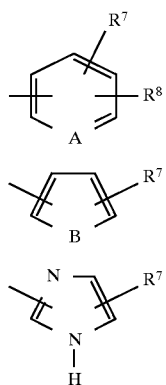

in which
A represents CH or nitrogen;
B represents oxygen, sulphur, NH or N-methyl; and
$R^7$ and $R^8$ independently represent hydrogen, halogen, cyano, trifluoromethyl, triazolyl, $C_{1-6}$ alkoxy, $C_{2-6}$ alkylcarbonyl, amino, $C_{1-6}$ alkylamino, di($C_{1-6}$) alkylamino, $C_{2-6}$ alkylcarbonylamino, $C_{1-6}$ alkylsulphonylamino, aminocarbonylamino or $C_{1-6}$ alkylaminosulphonylmethyl.

5. A compound as claimed in claim 1 represented by formula IIB, and salts and prodrugs thereof:

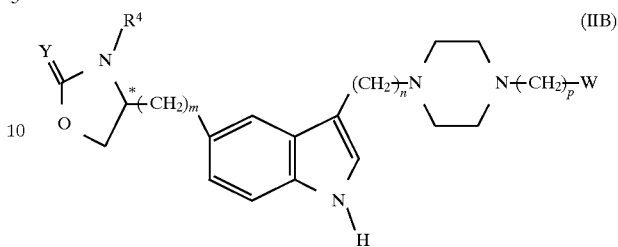

wherein the asterisk * denotes a chiral centre;
$R^4$ and Y are as defined in claim 1; and
m, n, p and W are as defined in claim 4.

6. A compound selected from:
1-[3-(5-(N-methylaminosulphonylmethyl)-1H-indol-3-yl) propyl]-4-[2-(4-(acetylamino) phenyl)ethyl]piperazine;
and salts and prodrugs thereof.

7. A compound selected from:
(S)-4-[3-(3-(4-(2-(3,4-difluorophenyl)ethyl)piperazin-1-yl) propyl)-1H-indol-5-ylmethyl]oxazolidin-2-one;
(S)-4-[3-(3-(4-(2-(3,4-difluorophenyl)ethyl)piperazin-1-yl) propyl)-1H-indol-5-ylmethyl]-3-methyloxazolidin-2-one;
and salts and prodrugs thereof.

8. A pharmaceutical composition comprising a compound as claimed in claim 1 in association with a pharmaceutically acceptable carrier.

9. A method for the treatment and/or prevention of clinical conditions for which a subtype-selective agonist of 5-$HT_{1D}$ receptors is indicated, which method comprises administering to a patient in need of such treatment an effective amount of a compound as claimed in claim 1.

* * * * *

UNITED STATES PATENT AND TRADEMARK OFFICE
CERTIFICATE OF CORRECTION

PATENT NO. : 5,854,247
DATED : December 29, 1998
INVENTOR(S) : Baker, et al.

It is certified that error appears in the above-identified patent and that said Letters Patent is hereby corrected as shown below:

Column 2, lines 35-43, and column 22, lines 3-11 delete

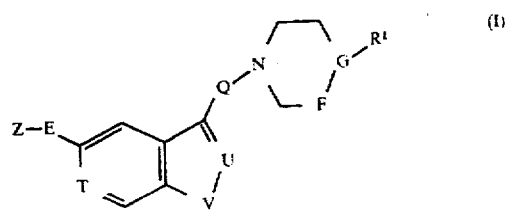

(I)

insert --

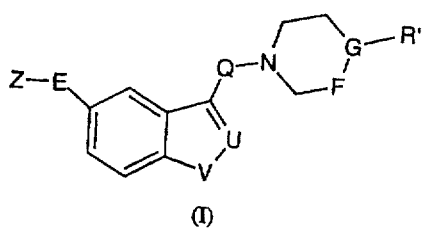

(I)

Signed and Sealed this

Sixteenth Day of February, 1999

Attest:

Attesting Officer

Acting Commissioner of Patents and Trademarks